United States Patent [19]

McCoy

[11] Patent Number: 5,165,402
[45] Date of Patent: Nov. 24, 1992

[54] THERAPEUTIC WRAP

[76] Inventor: Kevin McCoy, 3612 Double Rock La., Baltimore, Md. 21234

[21] Appl. No.: 692,918

[22] Filed: Apr. 29, 1991

[51] Int. Cl.$^5$ .................................................. A61F 7/00
[52] U.S. Cl. ......................................... 128/402; 602/2
[58] Field of Search .............. 128/399, 400, 402, 403, 128/165, 82.1, 24.1, DIG. 15, 160, 68.1, 169, 109.1, 111.1, 100.1, 101.1, 88; 62/530, 259.3; 165/46; 383/901; 606/201-204

[56] References Cited

U.S. PATENT DOCUMENTS

| | | | |
|---|---|---|---|
| 1,894,161 | 1/1933 | Crapo | 128/403 |
| 1,910,328 | 5/1933 | Glennan | 128/402 |
| 2,270,685 | 1/1942 | Miller | 128/165 |
| 3,075,517 | 1/1963 | Morehead | 128/402 |
| 3,678,936 | 7/1972 | McCormick . | |
| 4,081,150 | 3/1978 | Tyson | 128/402 |
| 4,092,982 | 6/1978 | Salem . | |
| 4,243,041 | 1/1981 | Paul . | |
| 4,441,493 | 4/1984 | Nirschl | 128/165 |
| 4,527,566 | 7/1985 | Abare . | |
| 4,586,506 | 5/1986 | Nangle . | |
| 4,628,918 | 12/1986 | Johnson, Jr. | 128/169 |
| 4,671,267 | 6/1987 | Stout . | |
| 4,972,832 | 11/1990 | Trapini et al. | 128/402 |

FOREIGN PATENT DOCUMENTS 36910 10/1981 European Pat. Off. ......... 128/82.11

*Primary Examiner*—Mark Graham
*Attorney, Agent, or Firm*—Baker & Botts

[57] ABSTRACT

A therapeutic wrap for the treatment of injuries having an elongated strip of stretchable material, a base connected to the elongated strip and formed of substantially non-stretchable material, two loops connected to the base for the attachment of the wrap and for the application of even pressure to the treated area, and may also contain a receptacle connected to the elongated strip to receive a cold or hot pack, a cold pack for the application of cold therapy to the treated area, mating fasteners attached to one side of the elongated strip to assist in the attachment of the therapeutic wrap.

5 Claims, 3 Drawing Sheets

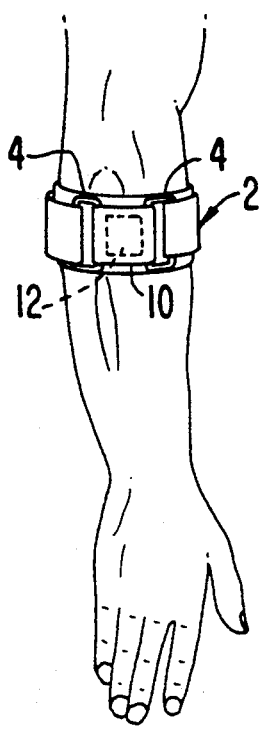
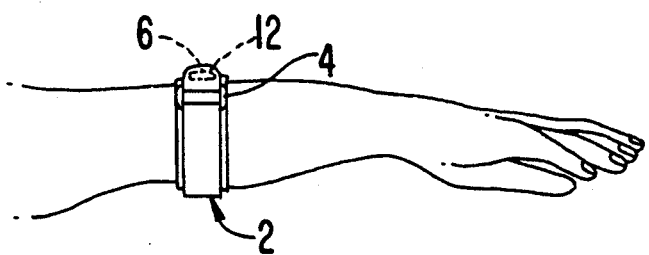
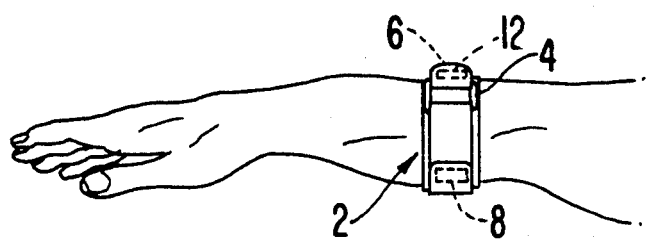
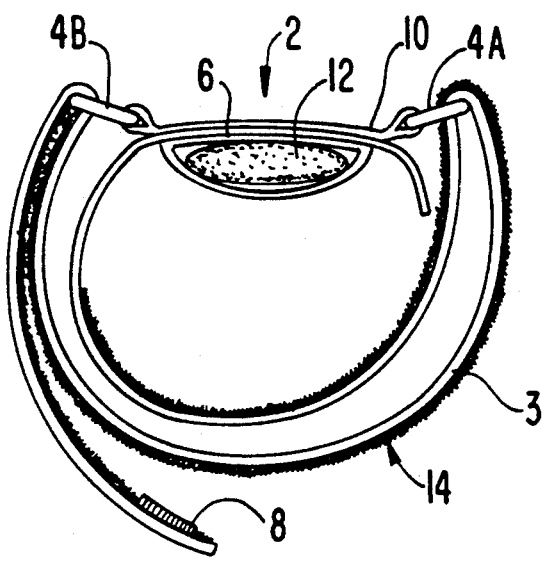

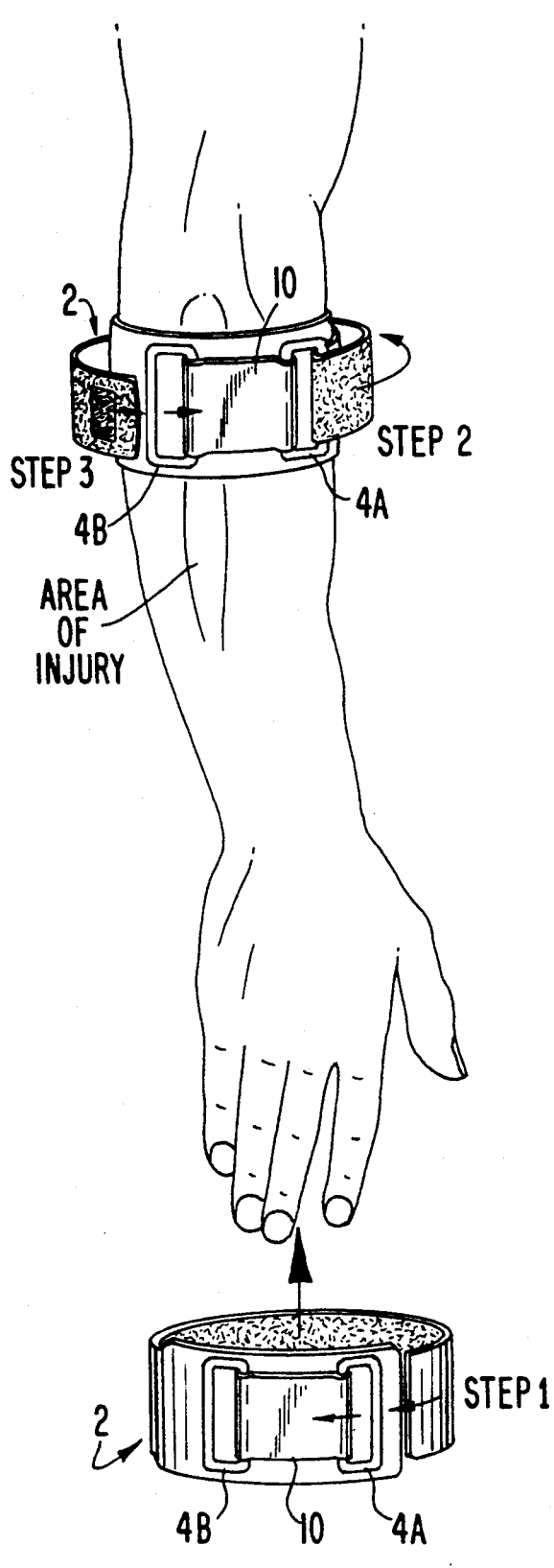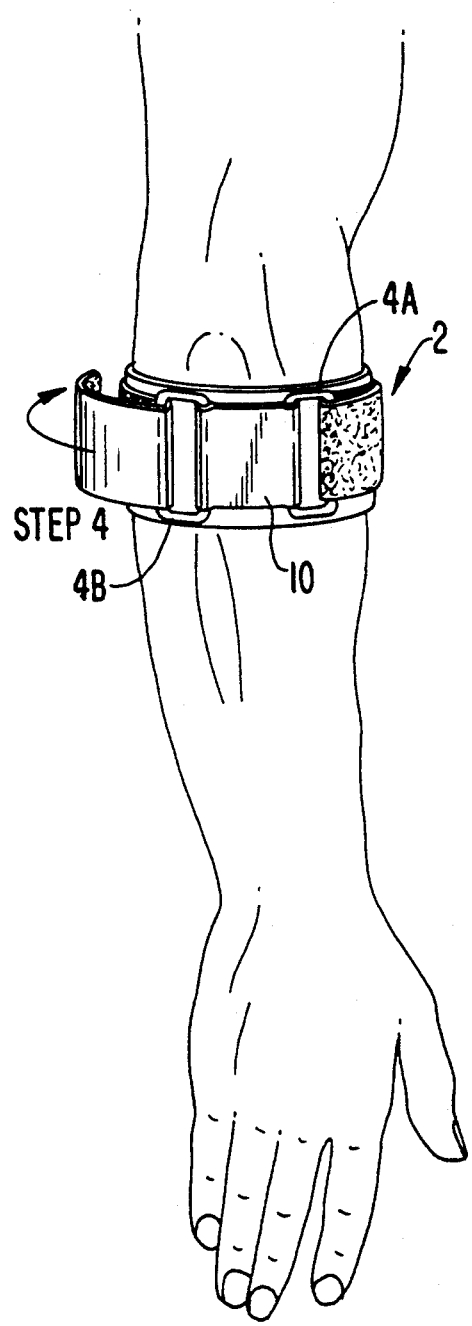

THERAPEUTIC WRAP

BACKGROUND OF THE INVENTION

The present invention generally relates to a therapeutic wrap for the treatment of injuries, and more particularly, to a therapeutic wrap having a two loop design and receptacle to receive a cold pack for the application of even pressure and cold therapy to an injured area.

There exists a variety of wraps, bandages and therapeutic devices for treating bruises, lacerations, strains or other injuries. A common injury among tennis players, baseball players and other sports enthusiasts is epicondylitis, or tennis elbow. Epicondylitis is an irritation or strain of the extensor muscles and tendons located near the forearm and elbow. In order to properly treat such an injury, direct even pressure and compression may be used to prevent the firing and thus the contraction of all irritated muscles in the forearm region. By preventing the firing of all extensor muscles, the injured muscles are given sufficient time to rest and heal. Furthermore, by preventing the firing and contraction of the muscles, much of the pain and discomfort associated with epicondylitis is temporarily eliminated. The application of cold therapy is also beneficial in the treatment of such injuries by enhancing the healing process through cold thickening of the blood and reducing swelling in the irritated area.

Prior art devices have implemented a variety of techniques in attempt to treat such injuries. These prior art devices may typically include a wrap having a pouch or pocket for receiving a cold pack, and may be attached using only hook and pile fasteners, or clips. U.S. Pat. No. 4,586,506 to Nangle discloses an elastic wrap which may receive a hot or cold pack. The wrap is attached using hook and pile type fasteners. However, Nangle does not allow the application of sufficient pressure to the irritated area to prevent the firing of muscles. A hook and pile fastener alone is sufficient to hold the cold pack adjacent to the irritated area, but is unable to withstand the tension necessary to apply the pressure and compression necessary to prevent the muscles from firing. Hook and pile fasteners by themselves are also prone to being accidentally released, thereby causing such wraps to be unreliable. In addition, wraps that pull from a single side or use a single loop apply pressure at an angle thereby inhibiting some of the muscles from firing while allowing others to operate and contract in a painful and destructive manner. This unequal tension may cause further irritation to the injured area due to the twisting effect across the forearm. Therefore, a need has arisen for a reliable therapeutic device that applies uniform direct pressure and cold therapy in order to more effectively treat musculoskeletal injuries.

SUMMARY OF THE INVENTION

Accordingly, it is an object of the present invention to provide a therapeutic wrap having a reliable fastener.

It is a further object of the present invention to provide a therapeutic wrap that applies a uniform direct pressure to an injured area.

It is yet a further object of the present invention to provide a therapeutic wrap which applies sufficient pressure to an area to prevent the firing of all injured muscles.

It is yet another object of the present invention to provide a therapeutic wrap that allows for the application of cold therapy to an injured area.

It is yet another object of the present invention to provide a therapeutic wrap which enhances the healing process of a musculoskeletal injury and reduces pain and discomfort.

In accordance with the present invention, a therapeutic wrap for the treatment of injuries is provided which includes an elongated strip of stretchable material having first and second sides, a base of substantially non-stretchable material coupled to the first side, first and second loops connected to the base of substantially non-stretchable material wherein the wrap is inserted through the loops to attach the wrap to a wearer, a resealable receptacle connected to the second side for receiving a cold pack, a cold pack to be removably inserted into the receptacle for the application of cold therapy to the wearer, a first fastener located on the second side, and a second fastener located on said second side wherein the second fastener mates with the first fastener to assist in attaching the wrap to the wearer.

BRIEF DESCRIPTION OF THE DRAWINGS

A more complete appreciation of the present invention and many of the attendant advantages thereof will be readily obtained as the invention becomes better understood by reference to the following detailed description when considered in connection with the accompanying drawings.

FIG. 5A is a top view of the therapeutic wrap illustrated in FIGS. 1 and 2.

FIG. 5B is an outside view of the therapeutic wrap illustrated in FIGS. 1 and 2.

FIG. 5C is an inside view of the therapeutic wrap illustrated in FIGS. 1 and 2.

FIG. 6 is a side view of the therapeutic wrap of FIGS. 1 and 2, and illustrates how the therapeutic wrap functions.

FIGS. 7A and 7B are top views of the therapeutic wrap of FIGS. 1 and 2, and illustrates how the therapeutic wrap functions.

DETAILED DESCRIPTION

Figure 1:
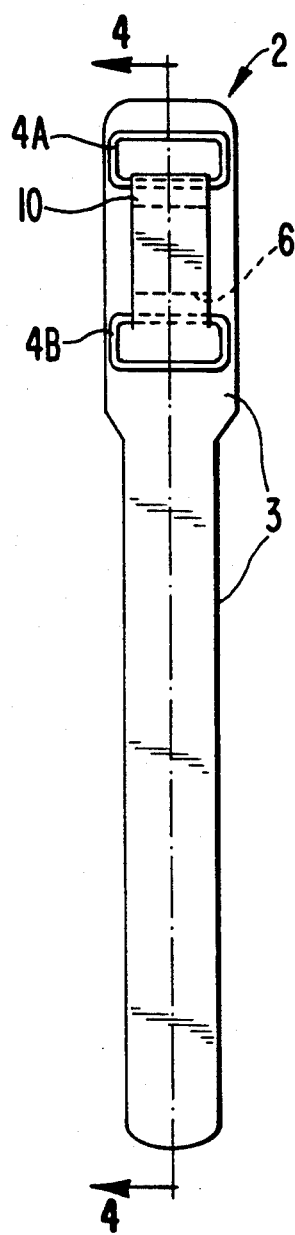
FIG. 1 is a top view of a therapeutic wrap according to the present invention.
Figure 2:
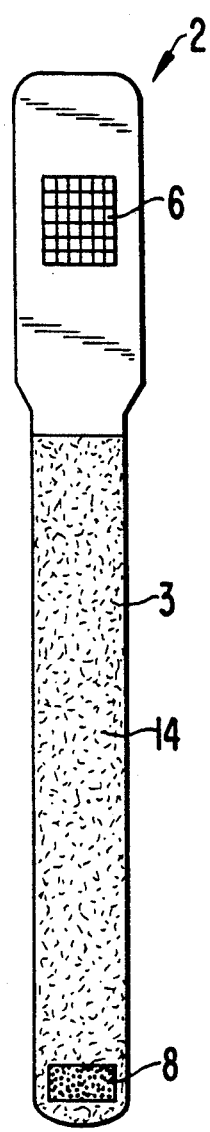
FIG. 2 is a bottom view of the therapeutic wrap illustrated in FIG. 1.
Figure 3:
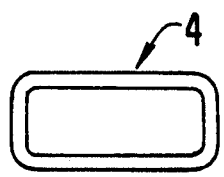
FIG. 3 is a diagram of a loop illustrated in FIG. 1.

Referring to the drawings in detail, wherein like numerals indicate like elements, FIG. 1 illustrates a therapeutic wrap according to the teachings of the present invention. Therapeutic wrap 2 comprises body 3 which is an elongated strip of flexible and stretchable material, preferably neoprene or the like. The use of neoprene or other stretchable material for body 3 provides the wearer with a snug and comfortable fit without restricting blood flow. Center base 10 is attached to body 3 and comprises a substantially non-stretchable material which is flexible, such as leather, naugahyde, plastic or other material. Center base 10 is preferably leather or naugahyde and is flexible enough to allow normal functional movement of areas not associated with the specifically treated area. However, center base 10 is preferably flexible enough not to restrict blood flow to the related areas, but is sufficiently non-stretchable to provide the needed direct pressure, compression and support to the treated area. Center base 10 is preferably sewn to body 3 but may be attached in a variety of ways such as glue, rivets, etc. Loops 4A and 4B (FIG. 3), are attached to the outer edges of center portion 10 and allow body 3 to be inserted through them to attach therapeutic wrap 2 to the wearer. Loops 4A and 4B are preferably formed of a substantially hard plastic, however, other materials such as metals, soft plastic, leather, etc. may also be used for this purpose. Loops 4A and 4B are preferably connected to center base 10 by wrapping an edge of center base 10 around each loop and then sewing the doubled layer of base 10, which is located inwardly from the loops 4A and 4B, to body 3. As illustrated in FIGS. 1 and 2, body 3 preferably tapers near loop 4B.

Figure 4:
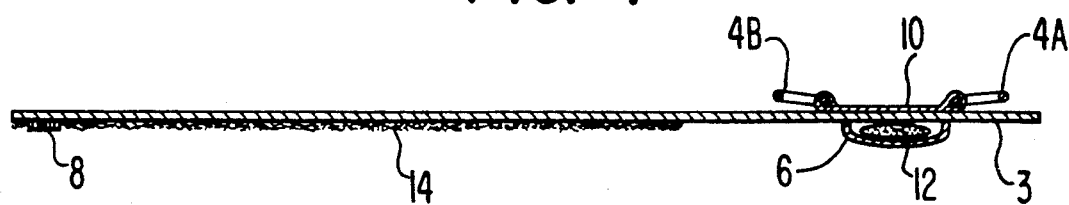
FIG. 4 is a sectional view taken generally along lines 4—4 of FIG. 1.

Referring to FIGS. 1, 2 and 4, therapeutic wrap 2 may also include receptacle 6 attached to body 3 on the side opposite from center portion 10 and loops 4. Receptacle 6 is a pouch or pocket and is preferably formed of a stretchable mesh material such as stretch nylon or the like. The stretchable material may be sewn or otherwise attached on three sides to body 3 to form receptacle 6 which can receive cold pack 12 through the fourth unsewn side. The unsewn side may have a fastener such as snaps, buttons, hook and pile fasteners, etc., to close receptacle 6 and prevent the escape of cold pack 12. However, because receptacle 6 is preferably formed of a stretchable material, receptacle 6 will fit tightly around cold pack 12 and thereby prevent its escape even without the use of a fastener located along the unsewn edge.

Therapeutic wrap 2 includes mating fasteners 8 and 14 attached to one side of body 3. Body 3 is inserted through loops 4A and 4B and therapeutic wrap 2 may be wrapped relatively snug around the wearer's arm to apply pressure and cold therapy to the forearm muscles for the treatment of epicondylitis or tennis elbow, as seen in FIGS. 5A-5C. Mating fasteners 8 and 14 are brought together to prevent therapeutic wrap 2 from loosening. Mating fasteners 8 and 14 are preferably hook and pile fasteners where fastener 14 is a strip of nylon brush attached to body 3, and fastener 8 is preferably a strip of hook material which connects to fastener 14. Fasteners 8 and 14 may also comprise other types of fasteners such as snaps, buttons, tape, etc.

Referring to FIGS. 6 and 7, therapeutic wrap 2 is shown in a functional position with body 3 inserted through both loops 4. To apply therapeutic wrap 2 to a specified area, the end of wrap 2 located closest to fastener 8 is wrapped around the injured area and fed through loop 4A. This allows the initial placement of wrap 2 and application of some pressure to the treated area. After going through loop 4A, therapeutic wrap 2 is wrapped back under the area and fed through loop 4B. By pulling the wrap through loop 4B, cold pack 12 and body 3 are pressed directly down on the irritated area. The use of just a single loop would cause the cold pack to be pressed down on the injured area at an angle, rather than straight down, which is much more desirable for effective treatment. The two loop design of the present invention allows an even tension from both sides of cold pack 12 and thus applies even pressure straight down on the injured area. Wrap 2 is then pulled tight and secured in place using fasteners 8 and 14 to prevent the loosening of wrap 2.

The present invention may be used to apply even pressure and also cold therapy to an injured or irritated area to reduce pain, swelling and discomfort. Therapeutic wrap 2 may, for example, be applied to the upper forearm to apply pressure and cold therapy to the extensor muscles and tendons to relieve much of the pain and discomfort associated with epicondylitis or tennis elbow as shown in FIGS. 5A-5C. Therapeutic wrap 2 is wrapped around the forearm and applies even pressure straight down on the injured area without twisting the forearm and avoids the uneven application of pressure applied by prior art devices which may pull from only one side. Because the two loop design of the present invention pulls equally from both right and left sides, cold pack 12 and body 3 are pressed straight down against the injured area to provide maximum therapeutic benefit. The application of pressure across the extensor muscles and tendons prevents the firing of these muscles. In this manner, the contraction and use of these irritated or strained muscles is inhibited so as to reduce the pain and discomfort associated with tennis elbow, or other injury. The application of pressure to irritated or strained muscles may also enhance the healing process by preventing the use of these muscles and giving the muscles sufficient rest for healing to occur and avoiding further injury. The application of even pressure across the injured area inhibits the firing of the muscles more uniformly and completely and thus more effectively relieves pain, discomfort and provides generally superior treatment than prior art devices. The present invention preferably contains receptacle 6 for the reception of a cold or hot pack. The present invention may alternatively be constructed without a receptacle for the application of even and direct pressure in order to prevent the firing and use of injured or irritated muscles and tissue and thereby decrease pain and discomfort.

The application of cold therapy to the injured area through the use of cold pack 12 reduces pain and swelling of the injured area. Cold therapy may also enhance the healing process through cold thickening of the blood. The design of the present invention which uses two loops and hook and pile fasteners allows sufficient tension to be applied to the injured area to prevent the firing of injured muscles, and provides a more reliable fastener combination than available in prior art.

Therapeutic wrap 2 may also be used to treat a variety of other injuries to muscles, ligaments, tendons, etc., including ankle, knee, shoulder, leg and other injuries.

This invention has been described in detail in connection with the preferred embodiments but is for illustrative purposes only and the invention is not limited thereto. It will be easily understood by those skilled in the art that variations and modifications can easily be made within the scope of this invention as defined by the appended claims.

I claim:

1. A therapeutic wrap for the treatment of injuries, said therapeutic wrap comprising:
   an elongated strip of stretchable material having first and second sides;
   a base of substantially non-stretchable material coupled to said first side;
   first and second loops connected to said base of substantially non-stretchable material wherein said wrap is insertable through said loops to attach the wrap to a wearer's arm and to apply even pressure straight down on an injured area in order to prevent firing and contraction of injured tissues;

a resealable receptacle connected to said second side for receiving a cold pack;

a cold pack to be removably inserted into said receptacle for the application of cold therapy to the wearer's arm;

a first fastener located on said second side; and a second fastener located on said second side wherein said second fastener mates with said first fastener to assist in attaching the wrap to the wearer.

2. A therapeutic wrap according to claim 1 wherein said base comprises leather.

3. A therapeutic wrap according to claim 1 wherein said first and second fasteners comprise hook and pile fasteners.

4. A therapeutic wrap according to claim 1 wherein said receptacle is formed of stretch nylon and which is sewn to said second side.

5. A therapeutic wrap according to claim 1 wherein said first and second loops are formed of plastic.

* * * * *